United States Patent [19]
Armitage

[11] Patent Number: 5,260,766
[45] Date of Patent: Nov. 9, 1993

[54] APPARATUS FOR DETECTION OF AN IMPERFECT SEAL AND METHOD THEREFORE

[76] Inventor: Mark H. Armitage, 793 Tioga Pl., Newbury Park, Calif. 91320

[21] Appl. No.: 862,078

[22] Filed: Apr. 2, 1992

[51] Int. Cl.$^5$ .................. G01N 21/88; G01N 21/89
[52] U.S. Cl. .................... 356/237; 356/239; 250/562; 219/10.53; 358/106
[58] Field of Search ............ 356/237, 239, 394, 371, 356/429, 430, 445, 448, 240; 250/571, 572, 222.2, 562, 223 B; 219/8.5, 10.53, 10.79, 4.91, 10.81, 10.57; 156/203, 323, 320; 426/107, 113, 234; 73/588, 865.8; 382/4, 8; 358/101, 106, 107

[56] References Cited

U.S. PATENT DOCUMENTS

| | | | |
|---|---|---|---|
| 3,941,485 | 3/1976 | Madden | 356/429 |
| 4,242,702 | 12/1980 | Kuni et al. | 356/394 |
| 4,496,819 | 1/1985 | Acker et al. | 219/10.53 |
| 5,184,190 | 2/1993 | Rai et al. | 356/239 |

Primary Examiner—Richard A. Rosenberger
Assistant Examiner—Hoa Q. Pham
Attorney, Agent, or Firm—Jack Munro

[57] ABSTRACT

An apparatus and method for detection of an imperfect seal between a plurality of plastic sheets. A transparent heated seal bar is tightly applied against the plurality of plastic sheets with the heat producing a welding between the sheets. A light source is projected into the seal bar with reflection occurring back through the seal bar from the seal area producing an image. This image is then picked up by a camera and transmitted to a visual analyzing computer which compares the produced seal to an image of a perfect seal and if significant differences are noted the computer causes activation of an annunciator to make known the creation of the imperfect seal.

9 Claims, 2 Drawing Sheets

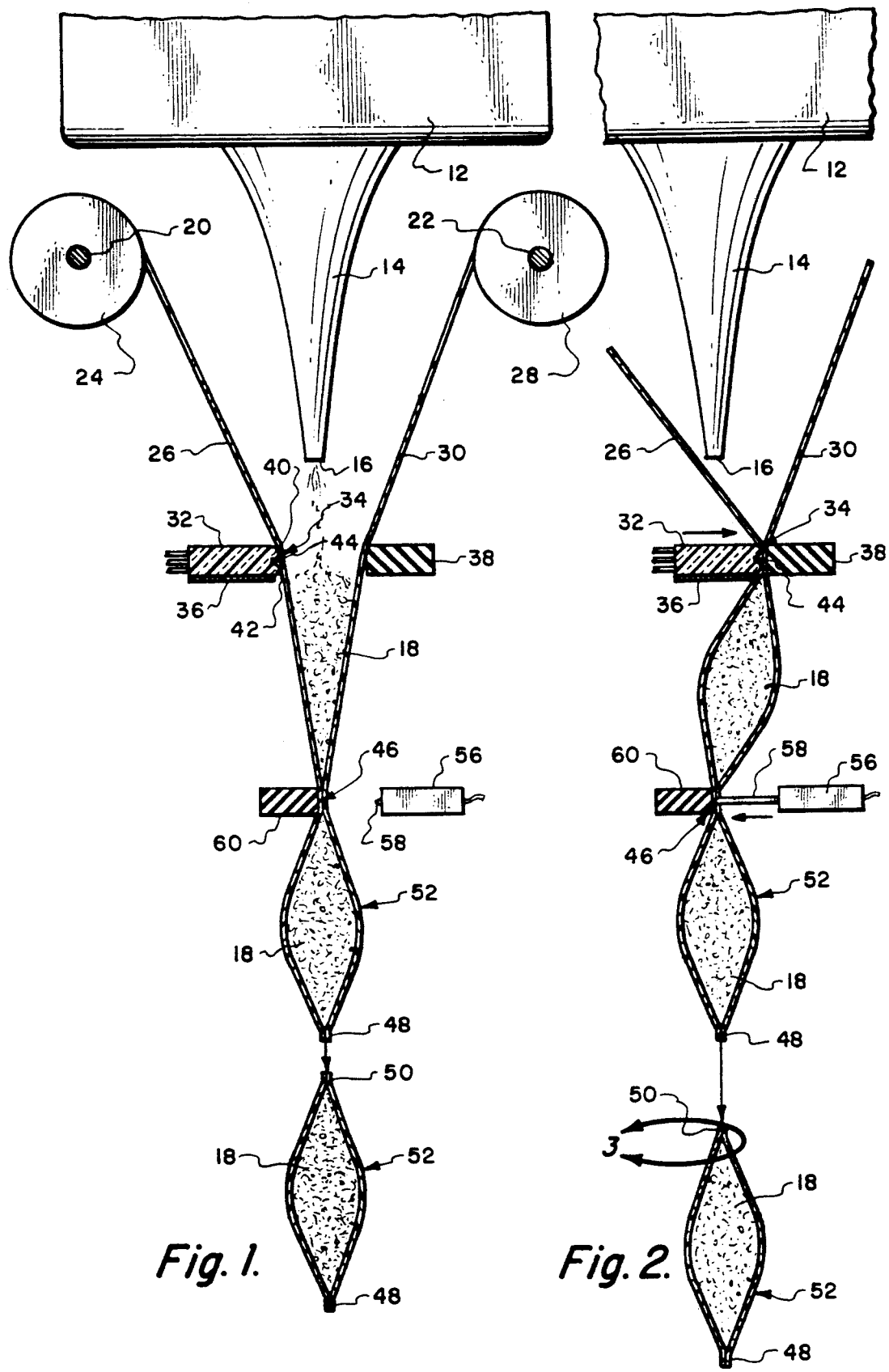

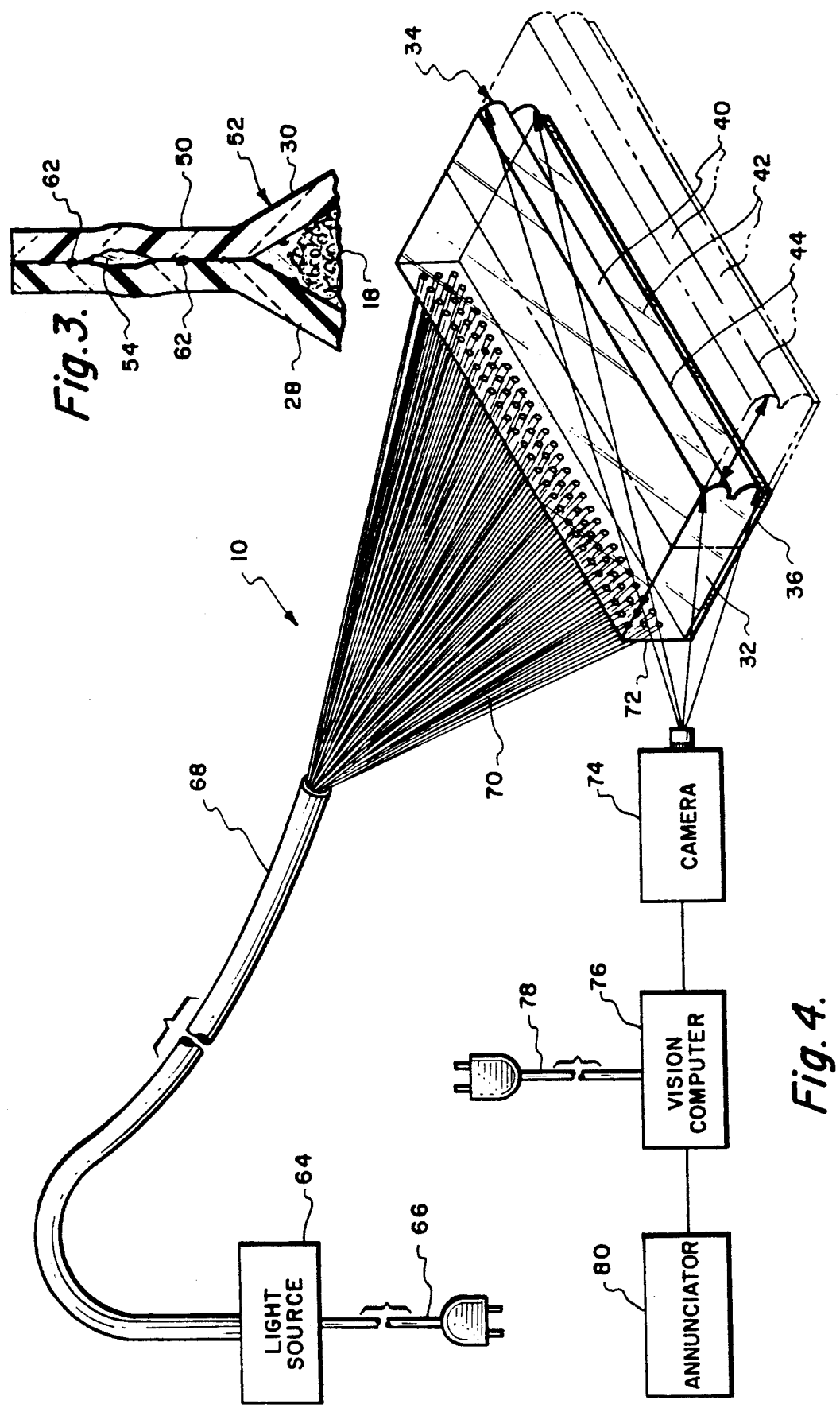

APPARATUS FOR DETECTION OF AN IMPERFECT SEAL AND METHOD THEREFORE

BACKGROUND OF THE INVENTION

1) Field of the Invention

The field of this invention relates to detection apparatuses and more particularly to an apparatus which is designed to detect the creation of a heat seal between a plurality of abutting plastic sheets.

2) Description of the Prior Art

The present invention has to do with the forming of seals between thin sheets of plastic. These seals are commonly formed to form plastic bags with these bags being filled with some substance. This filling of the bags is accomplished automatically with automatic bag filling equipment. Common types of such substances could be a powder liquid or a semi-liquid slurry. Within the food industry typical bags could be with a tomato sauce or tomato type of slurry.

Within the food industry, a tomato slurry would be formulated within a mixing vat. From the mixing vat, the tomato slurry is conducted to a hopper. On each side of the hopper there is moved a sheet material plastic, with underneath the hopper these plastic sheets abuttingly joining together. A sealing device is then to be used to seal the plastic sheets forming a horizontal seal with separate sealing devices being used to form vertical seals at the sides of the sheet material members. The net result is, a bag is formed and immediately after formulation of the bag a prescribed weighted amount of the slurry is discharged from the hopper into the now filled bag. The sheet material members are now moved a short distance and the resealing process continues forming another bag and so forth. After the bag is formed, sealed at both the upper and the lower ends, a cutter is used to separate each bag from its directly adjacent bag. The now separated bag is to be shipped to the desired location where the tomato slurry is to be utilized such as at a store that makes pizzas.

At times, during the heat sealing process, a small amount of residue of the tomato slurry may be located in the area where the heat sealing incurs. If such is the case, an imperfect seal will be produced. It is important to seal the bag from air to eliminate any possible generation of undesireable bacteria as well as premature deterioration of the food within the bag.

The automated equipment that is utilized in the generation of the bags of food produces such in a rather rapid manner. In the past, there have been utilized people whose job is to physically observe seals on the bags and make a determination if any bag has an imperfect seal. Such manual observation is effective for a short period of time. However, over a period of hours, the individual or individuals involved which do the observing become rather inefficient at discovering the imperfect seals. In the way that the bags are filled automatically there should be achieved some way to automatically ascertain whether the seals of the bags are satisfactory.

SUMMARY OF THE INVENTION

The structure of the present invention is utilized in conjunction with a hopper through which is discharged some form of a liquid slurry. Placed on either side of the hopper is a plastic sheet that is dispensed from a roll with it being understood that there are two in number of such sheets and two in number of such rolls. The plastic sheets actually physically abut one another just underneath a hopper through which the slurry is dispensed. The two plastic sheets are joined together by a heat sealing process-forming a bag with the horizontal seal at the bag being achieved by a transparent seal bar. This transparent seal bar is capable of optically transmitting light. This seal bar is connected to a fiber optic bundle and to a light source with light being substantially evenly distributed across the entire length of the seal bar. The light is directed through the seal bar to the sealing area with a portion of the light then being reflected from the sealing area back through the seal bar to be picked up by an array of cameras which are mounted directly adjacent but spaced from the back edge of the seal bar. The image from the camera array is then displayed within a visual command processor which compares the received image to an image of a satisfactorily obtained seal and compares such. If differences are perceived beyond a preprogrammed parameter of difference, the processor will then cause activation of an annunciator to announce that the bag, that has been just immediately filled has an imperfect seal. Typical forms of an annunciator could be a buzzer, a light, deactivation of the automatic filling equipment, etc.

The primary objective of the present invention is to construct an apparatus which will automatically ascertain the quality of a heat seal obtained between a plurality of thin plastic sheets or other similar type of sheet material members.

Another objective of the present invention is to eliminate errors that would occur naturally in the discovery of imperfect seals by manual observation.

Still another objective of the present invention is to construct an apparatus which can discover imperfect seals without requiring the employment of people to do so.

Another objective of the present invention is to construct an apparatus which automatically ascertains the quality of heat seal in a manner less expensively than employing individuals to do the same work.

BRIEF DESCRIPTION OF THE DRAWINGS

FIG. 1 is a schematic view of bag-forming equipment depicting the forming of substance-filled bags which will be a typical environment within which the present invention would be utilized and where the present invention is depicted in a non-sealing position and the cutter utilized to remove to separate filled bags is shown in the non-cutting position;

FIG. 2 is a view similar to FIG. 1 but showing the cutter in the cutting position and the sealing apparatus of the present invention in the sealing position;

FIG. 3 is an enlarged cross-sectional view through one of the seals formed to make a food-filled bag taken along line 3—3 of FIG. 2; and FIG. 4 is a schematic view showing the overall system of the apparatus of the present invention.

DETAILED DESCRIPTION OF THE SHOWN EMBODIMENT

Referring particularly to FIGS. 1 and 2, there is shown a typical environment where the apparatus 10 of the present invention could be utilized. In FIGS. 1 and 2 there is shown a food mixing hopper 12 which has a dispensing spout 14. Dispensing spout 14 terminates in a discharge opening 16 which is normally closed by a gate type of valve which is not shown. It is to be understood that from the discharge opening 16 a precise quantity by weight of the food 18 is to be dispensed from the spout 14.

Mounted on one side of the spout 14 is a roller 20. Mounted on the opposite side of the spout 14 is a second roller 22. Rotatably mounted on the roller 20 is a roll 24 of a sheet material plastic member 26. In a similar manner a roll 28 of a sheet material plastic member 30 is rotatably mounted on roller 22. Both of the members 26 and 30 will be of the same material and generally be in the range of two to six mils in thickness. The width of each of the members 26 and 30 is whatever is desired with generally a width of six inches to twelve inches being selected.

The members 26 and 30 are each to be fed to an area below the discharge opening 16 as is clearly shown in FIGS. 1 to 2. The members 26 and 30 are to be welded together by a heat seal bar 32 which has a sealing edge 34. This heat seal bar 32 is to be heated to an elevated temperature by a heating coil arrangement 36 which is mounted on the underside of the seal bar 32.

This seal bar 32 is to be movable against a fixed bar 38 tightly clamping together the members 26 and 30 in the area of the sealing surface 34. The sealing surface 34 is shown to have a horizontally disposed elongated convex upper surface 40 and a similar such lower surface 42. The surfaces 40 and 42 are separated by a crevice 44. When the seal bar 32 is pressed against the fixed bar 38 for a short period of time, such as a second or two, the seal bar 32 causes a welding to occur between the members 26 and 30 forming a seal 46. Convex upper surface 40 forms the upper section 48 of the seal 46 with the convex lower surface 42 forming the lower section 50 of the seal 46. Seal 48 seals the bottom of the resultingly formed bag 52 with seal 50 sealing the top of the bag 52. The groove 44 produces an unsealed area 54 separating the sealed areas 48 and 50.

It is to be understood that when the sealing bar 32 is moved in against the fixed bar 38, that the members 26 and 30 are momentarily stopped during the forming of this seal 46. At the same time, cutting mechanism 56 is activated which projects cutting blade 58 into contact with the unsealed area 54 cutting such separating the lowermost bag 52 in a series of formed bags. The cutting blade 58 will operate against a fixed bar 60.

Prior to moving of the seal bar 32, the members 26 and 30 move in unison in a downward direction away from discharge opening 16. A this occurs, foodstuff 18 is being discharged from the discharge opening 16 in the prescribed quantity which falls into the space occupied between the members 26 and 30. It is to be understood that there will occur at some point a side sealing of the bag 52. However, since the side sealing does not constitute any part of this invention it is not necessary to describe such in detail.

When the required quantity of foodstuff 18 has been deposited between the members 26 and 30, the members 26 and 30 will momentarily stop and the sealing bar 32 will be moved against the fixed bar 38 tightly pressing together members 26 and 30 with heat being applied by the seal bar 36 and welding of the members 26 and 30 will occur forming the seal 46. However, at times, although it is not intended for such to occur, there will be caused particles 62 of the foodstuff to be located within the area of the seals 48 and 50. In conjunction with this invention, the apparatus 10 is designed to determine if foodstuff has contaminated the top seal 50 rather than the bottom seal 48. However, it is considered to be within the scope of this invention that the apparatus 10 could be utilized also in conjunction with the bottom seal 48 if such is deemed to be desired. Still further, the apparatus 10 of this invention could be utilized in conjunction with the side seals of the bag 52 if such also is deemed to be desired.

If the particles 62 are located within the seal 50, that particular bag 52 needs to be removed from the production line, opened and the foodstuff 18 in that bag, placed back into the hopper 12 and that particular bag discarded. It is common for the bags 52, after they are produced, to immediately proceed to a freezer where the foodstuff 18 is to be frozen prior to being shipped to the consuming location. With the particles 62 located within the seal 50, the seal 50 is imperfect and air could potentially enter the interior of the bag 52. This is an undesireable occurrence since the air will cause the foodstuff 18 to spoil and therefore have to be discarded.

Normally, the ascertaining of an imperfect sealing within the seal 50 is accomplished manually. However, using the apparatus 10 of this invention, the seal bar 32 is constructed of an optically transparent material. A desireable material is sold under the trade name ZERODUR, manufactured by Schott Glass Technologies, Inc. of Duryea, Pennsylvania. This ZERODUR is a glass ceramic which is homogeneous, transparent and can be sawn, drilled, grinded and polished using standard glass processing methods. ZERODUR is preferred as it permits rapid changes in temperature without effecting its optical ability. ZERODUR is used within the present invention because of its precision reflective optic ability.

A light source 64 produces light within fiber optic bundle 68 electrically from electrical cord 66. The bundle 68 is composed of fiber optic threads 70. These threads 70 are optically adhesively secured to the back surface 72 of the heat seal bar 32. The light from the thread 70 is projected into the seal bar 32 directly toward convex member 42. A portion of this light is reflected back through the body of the seal bar 32 with this reflection to be picked up by an array of cameras 74. Within FIG. 4 of the drawing there is shown a single camera 74 but it is to be understood that there will be plurality of such cameras 74. Also in FIG. 4 the camera 74 is shown located at the side of the seal bar 32 when in fact the array of cameras 74 would be located along the back edge 72 beneath the connection of the threads 70. The location of the camera 74 in FIG. 4 is strictly for facilitating illustration.

The reflected light from the convex member 42 produces an image within each camera 74. With each camera 74 picking up a certain longitudinal length of the member 42. These images are combined within a vision computer 76. The images will detect the particle 6 since such will not reflect light in the same manner as the remaining portion of the seal 50. Within the vision computer 76, the reflected image is compared to what should be a perfect image of the seal 50 which has been preprogrammed into the vision computer 76. The vision computer 76 is to be operated electrically from electrical conduit 78. If the vision computer 76 detects an imperfect seal 50, an annunciator 80 is activated. Annunciator 80 can take any desired form such as a bell, a buzzer stopping of the movement of the members 26 and 30 or whatever is required to call attention to the fact that the seal 50 that was fast produced is imperfect. More than likely the annunciator 80 will take some form of a light or buzzer.

A desireable type of camera 74 would be model TM-540, miniature CCD Camera manufactured by PULNIX America, Inc. of Sunnyvale, Calif. This type of camera fits mounting within a very confined area since the camera is of an extremely small size. It is to be understood that the camera array 74 will be located a short-spaced distance from the back edge 72. Typically, four to six cameras 74 will be utilized.

The vision computer 76 is a 386-based high resolution, grey-scale, manufactured by INTELLEDEX, Inc. of Corvallis, Ore., model 386-HR computer. This type of vision computer can be programmed to capture, analyze and accept good sealing images or reject bad sealing images based on flexibly programmed tolerance data. This computer 76 can also facilitate the triggering of an output signal to a external reject mechanism which is in the form of the annunciator 80.

What is claimed is:

1. The method of detecting an imperfect weld joint between a plurality of thin sheet material members comprising the steps of:

placing the members in juxtaposition;

tightly squeezing said members together using a transparent seal bar which has been heated to a sufficiently raised temperature to cause localized melting of said members in the area of said seal bar and welding together of said members forming a seal;

observing of said seal through said seal bar;

ascertaining of any imperfection in said seal by discovering one or more hiatuses in said seal; and announcing the detection of an imperfect seal.

2. The method as defined in claim 1 wherein between said squeezing step and said observing step there is utilized the following step:

projecting light onto the area of said seal.

3. The method as defined in claim 2 wherein the step of observing is achieved by reflecting of a portion of the projected light from the area of said seal through said seal bar producing an optical image.

4. The method as defined in claim 3 wherein the step of ascertaining includes:

projecting of the image of the reflective light within a visual command processor and comparing of that image with the image of a perfect seal.

5. An apparatus for detection of an imperfect welding together of a plurality of thin sheet material members forming a seal, said apparatus comprising:

a transparent heated seal bar having a front edge tightly applied against said plurality of said thin sheet material members producing a welding therebetween;

light projection means connected to said seal bar for projecting light from a light source into said seal bar directed toward said front edge a portion of which reflects therefrom through said seal bar producing an image directly representative of the quality of said seal between said members;

visual means for receiving said image and detecting of an imperfect seal; and annunciator means for making known the detection of said imperfect seal.

6. The apparatus as defined in claim 5 wherein:

said seal bar having a back edge, said back edge being spaced furthest from said front edge, said light projection means being connected at said back edge.

7. The apparatus as defined in claim 6 wherein:

said light projection means including a fiber optic bundle being secured to said back edge.

8. The apparatus as defined in claim 5 wherein:

said visual means detecting of said imperfect seal by comparing said image to an image of a perfect seal.

9. The apparatus as defined in claim 5 wherein:

said thin sheet material members being plastic.

* * * * *